United States Patent
York et al.

(10) Patent No.: US 10,301,250 B2
(45) Date of Patent: *May 28, 2019

(54) NITRIDED MIXED OXIDE CATALYST SYSTEM AND A PROCESS FOR THE PRODUCTION OF ETHYLENICALLY UNSATURATED CARBOXYLIC ACIDS OR ESTERS

(71) Applicant: Lucite International UK Limited, Southampton (GB)

(72) Inventors: Ian Andrew York, Wilton (GB); Sabina Zieman, Wilton (GB)

(73) Assignee: LUCITE INTERNATIONAL UK LIMITED, Southhampton (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/188,349

(22) Filed: Jun. 21, 2016

(65) Prior Publication Data

US 2016/0297739 A1 Oct. 13, 2016

Related U.S. Application Data

(62) Division of application No. 13/805,413, filed as application No. PCT/GB2011/051195 on Jun. 24, 2011, now Pat. No. 9,399,210.

(30) Foreign Application Priority Data

Jul. 1, 2010 (GB) .................................. 1011092.2

(51) Int. Cl.
| | | |
|---|---|---|
| *C07C 67/343* | (2006.01) | |
| *C07C 51/353* | (2006.01) | |
| *B01J 23/18* | (2006.01) | |
| *B01J 23/20* | (2006.01) | |
| *B01J 27/16* | (2006.01) | |
| *B01J 27/18* | (2006.01) | |
| *B01J 27/24* | (2006.01) | |
| *B01J 37/03* | (2006.01) | |
| *C01B 21/097* | (2006.01) | |
| *C01B 21/082* | (2006.01) | |

(52) U.S. Cl.
CPC ............ *C07C 67/343* (2013.01); *B01J 23/18* (2013.01); *B01J 23/20* (2013.01); *B01J 27/16* (2013.01); *B01J 27/1811* (2013.01); *B01J 27/1813* (2013.01); *B01J 27/24* (2013.01); *B01J 37/036* (2013.01); *C01B 21/0821* (2013.01); *C01B 21/097* (2013.01); *C07C 51/353* (2013.01)

(58) Field of Classification Search
CPC .. C07C 51/353; C07C 67/343; B01J 27/1811; B01J 27/24; B01J 23/18; B01J 27/16
See application file for complete search history.

(56) References Cited

U.S. PATENT DOCUMENTS

| | | | |
|---|---|---|---|
| 4,118,588 A | 10/1978 | Fouquet et al. | |
| 4,324,908 A | 4/1982 | Grasselli et al. | |
| 4,560,790 A | 12/1985 | Ryu | |
| 4,792,620 A * | 12/1988 | Paulik .................. | B01J 31/0231 560/232 |
| 9,399,210 B2 * | 7/2016 | York ....................... | B01J 23/18 |
| 2003/0009058 A1 | 1/2003 | Canos et al. | |
| 2006/0025604 A1 * | 2/2006 | Hutchenson ............ | B01J 23/02 549/263 |

FOREIGN PATENT DOCUMENTS

| | | |
|---|---|---|
| CN | 1382523 A | 12/2014 |
| EP | 1243574 A1 | 9/2002 |
| FR | 2743796 A1 | 7/1997 |
| JP | 200521312 A | 8/2005 |
| JP | 2005213182 A | 8/2005 |
| JP | 2005213182 A * | 8/2011 |
| WO | 95/21123 A1 | 8/1995 |
| WO | 95/23131 A1 | 8/1995 |
| WO | 9521123 A1 | 8/1995 |
| WO | 03053913 A1 | 7/2003 |
| WO | 2008/017338 A2 | 2/2008 |

OTHER PUBLICATIONS

Ai, Journal of Catalysis, Vapor-phase aldol condensation of formaldehyde with acetic acid on V2O5—P2O5 catalysts, 1987, 107(1), pp. 201-208.*
Wikipedia, Wikipedia, Nonmetal, recovered from https://en.wikipedia.org/wiki/Nonmetal#Applicable_elements on Oct. 25, 2017, pp. 1-20. (Year: 2017).*
Ebbinghaus et al, Progress in Solid State Chemistry, Perovskite-related oxynitrides—Recent developments in synthesis, characterisation and investigations of physical properties, 2009, 37, pp. 173-205. (Year: 2009).*
Grange et al, Preparation of Catalysts VI, Scientific Bases for the Preparation of Heterogeneous Catalysts A New Strong Basic High Surface Area Catalyst: The Nitrided Aluminophosphate: AlPON and Ni-AlPON, 1995, pp. 381-389. (Year: 1995).*
Fripiat et al (Journal of the European Ceramic Society, Synthesis and Characterization of a New Oxynitride Catalyst: The ZrPON Solids, 1997, 17, pp. 2011-2015. (Year: 1997).*
Grange et al, Preparation of Catalysts VI, Scientific Bases for the Preparation of Heterogeneous Catalysts a New Strong Basic High Surface Area Catalyst: The Nitrided Aluminophosphate: AlPON and Ni AlPON, 1995, pp. 381-389.

(Continued)

*Primary Examiner* — Paul A Zucker
(74) *Attorney, Agent, or Firm* — Shumaker, Loop & Kendrick, LLP

(57) ABSTRACT

A method of producing an ethylenically unsaturated carboxylic acid or ester, preferably an α, β ethylenically unsaturated carboxylic acid or ester. The method includes contacting formaldehyde or a suitable source thereof with a carboxylic acid or ester in the presence of a catalyst and optionally in the presence of an alcohol. The catalyst includes a nitrided metal oxide having at least two types of metal cations, $M^1$ and $M^2$, wherein $M^1$ is selected from the metals of group 2, 3, 4, 13 (called also IIIA) or 14 (called also IVA) of the periodic table and M2 is selected from the metals of groups 5 or 15 (called also VA) of the periodic table.

8 Claims, No Drawings

(56) References Cited

OTHER PUBLICATIONS

Fripiat et al., Journal of the European Ceramic Society, Synthesis and Characterization of a New Oxynitride Catalyst: The ZrPON Solids, 1997, 17, pp. 2011-2015.
White et al (Basic Energy Sciences Advisory Committee Subpanel Workshop Report, Opportunities for Catalysis in the 21st Century, 2002, pp. 1-47).
UK Search Report for GB 1011092.2 dated Apr. 18, 2011.
IPER from International Bureau for PCT/GB2011/051195 dated Jan. 8, 2013.
ISR and Written Opinion for PCT/GB2011/051195 dated Oct. 3, 2011.
K. Borszeky et al. "Enantioselective hydrogenation of alpha, beta-unsaturated acids. Substrate-modifier interaction over cinchonidine modified Pd/Al2O3," Tetrahedron Asymmetry, Nov. 27, 1997, pp. 3745-3753, vol. 8, No. 22, Pergamon Press, Ltd., Oxford, GB.
Isabel Di Cosimo, "Aldol Reaction—Heterogeneous," Encyclopedia of Catalysis, Mar. 5, 2010, pp. 1-16.
Ebbinghaus, S G et al., "Perovskite-related oxynitrides recent developments in synthesis, characterisation, and investigations of physical properties," Progress in Solid State Chemistry, Dec. 1, 2009, pp. 173-205, vol. 37, No. 2-3, Pergamon Press, Oxford, GB.
Peltier V, et al. "A novel family of mixed gallium aluminum phosphorus oxynitrides: their synthesis, characterization and utilization in heterogeneous catalysis," Materials Science and Engineering B47, Jun. 15, 1997, pp. 177-183, vol. 47, No. 2, Elsevier, Sequoia, Lausanne, CH.
Wiame H, et al. "Synthesis and Characterisation of a Novel Aluminovanadate Oxynitride Basic Catalyst" Journal of the European Ceramic Society, Jan. 1, 1997, pp. 2017-2020, vol. 17, No. 15-16, Elsevier Science Publishers, Barking, Essex, GB.
European Office Action for Application No. 11729662.4-1270 dated Feb. 8, 2013.
Office Action for Indian Patent Application No. 2701/MUMNP/2012 dated Jan. 10, 2018 (6 pages).
Fioravanti et al. "Facile and Highly Stereoselective One-Pot Synthesis of Either (E)- or (Z)-Nitro Alkenes", Org. Letter, vol. 10, No. 7, p. 1449-1451 (2008) (Abstract Only).

* cited by examiner

NITRIDED MIXED OXIDE CATALYST SYSTEM AND A PROCESS FOR THE PRODUCTION OF ETHYLENICALLY UNSATURATED CARBOXYLIC ACIDS OR ESTERS

RELATED APPLICATIONS

This U.S. Non-Provisional Application is a Divisional Application of and claims priority from U.S. Non-Provisional patent application Ser. No. 13/805,413 filed on Mar. 1, 2013 and issued as U.S. Pat. No. 9,399,210 on Jul. 26, 2016, which claims priority from PCT/GB2011/051195 filed on Jun. 24, 2011, which claims priority from GB Application 1011092.2 filed on Jul. 1, 2010. Each of the above mentioned Applications are herein incorporated by reference in its entirety

TECHNICAL FIELD AND BACKGROUND OF THE INVENTION

The present invention relates to nitrided mixed oxide catalysts and a process for the production of ethylenically unsaturated carboxylic acids or esters, particularly α, β unsaturated carboxylic acids or esters, more particularly (alk)acrylic acids or alkyl (alk)acrylates such as (meth) acrylic acid or alkyl (meth)acrylates by the condensation of carboxylic acids or esters with a methylene or ethylene source, such as formaldehyde or a suitable source thereof in the presence of nitrided mixed oxide catalysts. In particular, but not exclusively, the invention relates to a process for the production of (meth) acrylic acid or alkyl esters thereof, for example, methyl methacrylate, by the condensation of propionic acid or alkyl esters thereof with formaldehyde or a source thereof in the presence of such nitrided mixed oxide catalysts.

SUMMARY OF THE INVENTION

Such acids or esters can be considered as being produced formulaically by reacting an alkanoic acid (or ester) of the formula $R^3$—$CH_2$—$COOR^4$, where $R^3$ and $R^4$ are each, independently, a suitable substituent known in the art of acrylic compounds such as hydrogen or an alkyl group, especially a lower alkyl group containing, for example, 1-4 carbon atoms, with a suitable methylene source, for example, a source of formaldehyde. Thus, for instance, methacrylic acid or alkyl esters thereof, especially methyl methacrylate, may be made by the catalytic reaction of propionic acid, or the corresponding alkyl ester, e.g. methyl propionate, with formaldehyde as a methylene source in accordance with the reaction sequence 1.

and

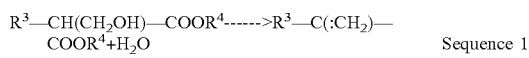  Sequence 1

An example of reaction sequence 1 is reaction sequence 2

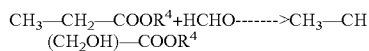

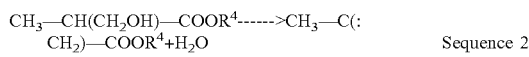  Sequence 2

The above reaction Sequence 1 or 2 is typically effected at an elevated temperature, usually in the range 250-400° C., using an acid/base catalyst. Where the desired product is an ester, the reaction is preferably effected in the presence of the relevant alcohol in order to minimise the formation of the corresponding acid through hydrolysis of the ester. Also for convenience it is often desirable to introduce the formaldehyde in the form of formalin. Hence, for the production of methyl methacrylate, the reaction mixture fed to the catalyst will generally consist of methyl propionate, methanol, formaldehyde and water.

Conventionally, methyl methacrylate has been produced industrially via the so-called acetone-cyanohydrin route. The process is capital intensive and produces methyl methacrylate at a relatively high cost.

U.S. Pat. No. 4,560,790 describes the production of α, β unsaturated carboxylic acids and esters by the condensation of methylal with a carboxylic acid or ester using a catalyst of general formula $M^1/M^2/P/O$ wherein $M^1$ is a group IIIb metal, preferably aluminium, and $M^2$ is a group IVb metal, preferably silicon.

Sumitomo have disclosed metal oxynitride catalysts for the preparation of α,β-unsaturated products using formaldehyde, JP 2005-213182A, nitriding single metal oxides such as $Ta_2O_5$ by thermal treatment with ammonia. The resultant oxynitrides catalysed the gas-phase condensation of formaldehyde (trioxane source) with propionic acid to methacrylic acid. Sumitomo also disclose the possibility of putting these single metal oxides on a support such as silica or alumina.

EP 1 243 574 discloses the use of Aluminium phosphates, silicoaluminophosphates and mesoporous amorphous alumina-silica and their nitrided or oxynitrided equivalents to catalyse the mixed aldol condensation of an n-alkylaldehyde and benzaldehyde to α-n-amylcinnamaldehyde. No noticeable improvement for the nitrided catalysts was found or taught. There is no disclosure of the use of a support. In fact, an increase in the yield of side products was noted for the nitrided catalysts.

As mentioned above, a known production method for MMA is the catalytic conversion of methyl propionate (MEP) to MMA using formaldehyde. A suitable catalyst for this is a caesium catalyst on a support, for instance, silica.

The inventors have analysed for comparison the effect of nitriding the silica support. Unmodified silica is effectively inert in the condensation reaction between formaldehyde and propionic acid to produce MMA. Nitridation of the silica introduced a very low activity, giving small yields of MMA and methacrolein. The catalytic performance of nitrided silica was very similar to that of silicon nitride ($Si_3N_4$), which has a hydrated surface analogous to that of silica. Therefore, compared to Cs impregnated silica, nitrided silica is not suitable for use in the condensation reaction between formaldehyde and a carboxylic acid or ester to produce MMA.

However, it has now been found that a particular combination of metal oxidation states in a mixed metal oxide that has been nitrided can provide a surprisingly high selectivity for the ethylenically unsaturated carboxylic acids or ester product in the reaction of a methylene or ethylene source such as formaldehyde, or a suitable source thereof with a carboxylic acid or ester to produce ethylenically unsaturated carboxylic acids or esters, particularly α, β ethylenically unsaturated carboxylic acids or esters.

According to a first aspect of the present invention there is provided a method of producing an ethylenically unsaturated carboxylic acid or ester, preferably an α, β ethylenically unsaturated carboxylic acid or ester, comprising the steps of contacting formaldehyde or a suitable source thereof with a carboxylic acid or ester in the presence of a catalyst and optionally in the presence of an alcohol, wherein the catalyst comprises a nitrided metal oxide having at least two types of metal cations, $M^1$ and $M^2$, wherein $M^1$ is selected from the metals of group 2, 3, 4, 13 (called also IIIA) or 14 (called also IVA) of the periodic table and $M^2$ is selected from the metals of groups 5 or 15 (called also VA) of the periodic table.

It will be appreciated by the skilled person that the invention is distinct from the existence of an incidental molecular monolayer of a nitrided single metal oxide catalyst formed on a support of another metal oxide. However, for the avoidance of doubt, typically, the catalyst cations, $M^1$ and $M^2$, and oxide and nitride anions are uniformly distributed throughout the nitrided metal oxide catalyst which catalyst extends to multiple molecular layers, more typically, at least 2 nm, most typically, at least 5 nm, especially, at least 10 nm average thickness. This would not be the case with a single nitrided metal oxide layer on a support where the metal of the support only interacts at the level of the catalyst molecular monolayer on the support (typically, about 1 nm thick) and not throughout the catalyst. Furthermore, in the invention, the metal cations, $M^1$ and $M^2$ and the oxide and nitride of the catalyst are exclusively from the catalyst and not from a support for the catalyst. Thus, in general, the catalyst of the invention is not a molecular monolayer on a support for the catalyst but a multi-layered catalyst having the properties defined in the invention throughout its substance.

Thus, in general, the cations or anions forming the nitrided metal oxide catalyst are not simultaneously metal cations or anions of a catalytic support unless, independent of the support, the catalyst is in accordance with the invention throughout its substance.

Typically, the nitrided metal oxide of the present invention exists and is used independently of any catalytic support. However, when used on a support, the nitrided mixed metal oxide provides a nitrided mixed metal oxide catalytic surface having $M^1$ type and $M^2$ type cations and oxygen and nitrogen anions independently of any metal cations and oxygen or nitrogen anions forming or contributed by the support.

According to a second aspect of the present invention there is provided a catalyst system for the reaction of formaldehyde or a suitable source thereof with a carboxylic acid or ester, optionally in the presence of an alcohol, to produce an ethylenically unsaturated carboxylic acid or ester, preferably α, β ethylenically unsaturated carboxylic acids or esters, wherein the catalyst comprises a nitrided metal oxide having at least two types of metal cations, $M^1$ and $M^2$, wherein $M^1$ is selected from at least two metals of group 2, 3, 4, 13 (called also IIIA), 14 (called also IVA) of the periodic table and $M^2$ is selected from at least one metal of group 5 or at least one metal of group 15 (called also VA) in the $4^{th}$ to $6^{th}$ periods of the periodic table.

In addition to the high selectivity achieved by the catalysts of the present invention, use of the catalyst of the present invention has been found to produce remarkably low levels of unwanted side products in the reaction of formaldehyde or a suitable source thereof with a carboxylic acid or ester to produce an ethylenically unsaturated carboxylic acid or ester. In particular, remarkably low levels of methyl isobutyrate (MIB), toluene and diethyl ketone compared to conventional catalysts such as aluminium phosphate. In addition, the catalysts provide excellent activity.

The present invention thus advantageously provides a successful method of improving the selectivity of strongly acidic catalysts. The high selectivity (up to 95%) obtained with the nitrided catalysts indicates that acid-type catalysis can provide viable ethylenically unsaturated carboxylic acid or ester selectivity.

Preferably, the nitrided mixed oxide is prepared by nitriding the mixed oxide. Typically, short nitridation treatments of between 3 and 15 hours are found to be effective in the nitridation of the catalytic surface. However, shorter or longer nitridations can be carried out depending on the nitridation conditions and substrates.

Preferably, the nitrided mixed oxide consists of two to four metal cations, and oxygen and nitrogen anions.

A preferred formula for the mixed oxide is therefore $M^1_x M^2_y O_n$ wherein $M^1$ is one or more 2+, 3+ or 4+ cations and $M^2$ is a 5+ cation wherein x is the number of $M^1$ atoms, y is the number of $M^2$ atoms and n is the number of oxygen atoms. Thus the nitrided metal oxide may be given by formula $M^1_x M^2_y O_n N_z$ wherein z is the average number of nitrogen atoms and wherein x, y, n and z may each be a decimal number or positive integer. Generally, x, y, n and z may independently be between 0.1 and 20, more preferably, between 0.1 and 10, most preferably, between 0.1 and 5. In a particularly preferred formula x and y are both 1 and n and z are numbers which provide the anionic balance to the cationic charge of $M^1$ and $M^2$.

Typically, the $M^1$ type of metal may be selected from one or more metals in the list consisting of:—Be, Mg, Ca, Sr, Ba, Ra, B, Al, Ga, In, Tl, Sc, Y, La, Ac, Si, Ge, Sn, Pb, Ti, Zr, Hf, Rf more preferably, Al, Ga or La, most preferably, Al.

Typically, the $M^2$ type of metal in the process of the present invention may be selected from one or more metals in the list consisting of:—P(5+), Nb(5+), As (5+) Sb(5+), or Ta(5+), more preferably, P(5+), Nb(5+) or Sb(5+), most preferably, P(5+). Typically, the $M^2$ type of metal in the catalyst invention of the second aspect of the present invention may be selected from one or more metals in the list consisting of: —Nb(5+), As (5+) Sb(5+) or Ta(5+), more preferably, Nb(5+) or Sb(5+), most preferably, Nb(5+).

Advantageously, using a mixture of metals of the type $M^1$ gives more flexibility in modifying the acid-base balance of the catalyst. In particular, a further $M^1$ metal can be introduced to provide an increase or decrease in acidity as appropriate. Preferred $M^1$ modifier metals for this purpose are barium and lanthanum.

Preferably, $M^1$ is/are cation(s) in the 3+ oxidation state. Preferably, $M^2$ is a cation in the +5 oxidation state.

Assuming nitrogen is not a metal, said metal cations of the type $M^1$ and $M^2$, whether one or more of each type is present, may form from 90 to 100 mol % of the total metal present in the mixed metal oxide, more especially, 95-100 mol %, most especially, 97-100 mol %, particularly, substantially 100 mol %. If another metal of the type $M^3$ set out below is present and/or another metal type, the metals of the type $M^1$ and $M^2$ may form up to 99.99 or 99.89 or 99.90 mol % of the total metal present, more typically, up to 99.90 or 99.80 mol % of the total metal present in the metal oxide with the same lower limits as already set out above.

Preferably, oxygen and nitrogen may form from 50 to 100 mol % of the total non-metal present in the metal oxide of the invention, more preferably, 70-100 mol % of the total non-metal present in the metal oxide, most preferably, 80-100 mol % of the total non-metal present, especially, 90-100 mol % of the total non-metal present in the metal oxide, more especially, 99%-100 mol %, most especially, substantially 100 mol %.

For the avoidance of doubt, non-metals herein does not include the "metalloid" elements boron, silicon, phosphorus, germanium, arsenic, antimony, tellurium and polonium but includes all elements having higher atomic numbers than the named element(s) in their respective period of the periodic table.

Preferably, the nitrided metal oxide forms 50-100 wt % of the catalyst, more preferably, 80-100 wt %, most preferably, 90-100 wt %, especially, 95-100 wt %, more especially, 97-100 wt %, most especially, 99-100 wt % of the catalyst. The balance of the catalyst is made up of impurities, binders or inert materials. Generally, the nitrided metal oxide forms about 100% of the catalyst.

However, when a binder is used in the present invention it may form up to 50 wt % of the catalyst. Alternatively, the binder may be used in conjunction with a catalyst support to bind the catalyst to the support. In the latter case, the binder does not form part of the catalyst as such.

Suitable binders for the catalyst of the present invention will be known to those skilled in the art. Non-limiting examples of suitable binders include silica (including colloidal silica), silica-alumina, such as conventional silica-alumina, silica-coated alumina and alumina-coated silica, and alumina, such as (pseudo)boehmite, gibbsite, titania, titania-coated alumina, zirconia, cationic clays or anionic clays such as saponite, bentonite, kaolin, sepiolite or hydrotalcite or mixtures thereof. Preferred binders are silica, alumina and zirconia or mixtures thereof.

The nitrided metal oxide particles can be embedded in the binder or vice versa. Generally, when used as part of the catalyst, the binder functions as an adhesive to hold the particles together. Preferably, the particles are homogeneously distributed within the binder or vice versa. The presence of the binder generally leads to an increase in mechanical strength of the final catalyst.

The typical average surface area of the metal oxide catalyst is in the range 2-1000 $m^2\ g^{-1}$, more preferably, 5-400 $m^2\ g^{-1}$, most preferably, 10-300 $m^2\ g^{-1}$ as measured by the B.E.T. multipoint method using a Micromeritics TriStar 3000 Surface Area and porosity Analyser. The reference material used for checking the instrument performance is a carbon black powder supplied by Micromeritics with a surface area of 30.6 $m^2/g$ (+/−0.75 $m^2/g$), part number 004-16833-00.

The typical average particle size of the catalyst particles is in the range 2 nm-10000 nm (10μ), more preferably, 5 nm-4000 nm (4μ), most preferably, 10 nm-3000 nm (3μ) as measured by a Malvern Zetasizer Nano S using dynamic light scattering and using NIST standards.

If the material is porous, it is preferably mesoporous with an average pore size of between 2 and 50 nm. Pore size can be determined by mercury intrusion porosimetry using NIST standards.

The average pore volume of the catalyst particles may be less than 0.01 $cm^3/g$ but is generally in the range 0.01-2 $cm^3/g$ as measured by nitrogen adsorption. However, microporous catalysts are not the most preferred because they may inhibit movement of reagents through the catalyst and a more preferred average pore volume is between 0.3-1.2 $cm^3/g$ as measured by BET multipoint method using nitrogen adsorption according to ISO 15901-2:2006. The Micromeritics TriStar Surface Area and Porosity Analyser is used to determine pore volume as in the case of surface area measurements and the same standards are employed.

In the case of a non supported catalyst, the nitrided metal oxide may be used directly in the form of a catalyst particles either free flowing or together with a suitable binder to create a solid of the desired shape and/or size. The particles may be of any suitable size and therefore also in the form of powder, granules or beads either with or without binder. Typically, the catalyst is used in the form of a fixed bed and for this purpose may be used alone or on a support and in the latter case may include a suitable catalytic binder to bind it to the support.

However, it is also possible for the catalyst to be used on a support. In this case, the nitrided metal oxide catalyst may form a suitable surface coating on a suitable support for a catalyst.

For the purposes of the present invention, the support does not form part of the catalyst.

Preferred combinations of nitrided metal oxides for use in the present invention may be selected from the list consisting of: —AlPON; ZrPON; SnPON; ZrNbON; GaSbON; and GaAlPON. These oxides are either unsupported or supported on a suitable support, for example, alumina, silica, silicon nitride, colloidal silica, titania or aluminium phosphate.

It will be understood by the skilled person that a catalyst of the invention may be added to a support by any suitable means. The catalyst may be fixed, preferably by calcination, onto a suitable support after deposition of the compound onto the support using a suitable salt in a suitable solvent and subsequent drying of the surface coated support. Alternatively, the catalyst or suitable catalyst salt precursors may be co-precipitated with the support or suitable support precursors such as a silica sol from a suitable solvent. Preferably, an oxide support is used, more preferably, an oxide support as mentioned herein.

It is also possible to use the catalyst of the present invention in a mixture or admixture with another catalyst according to the present invention or otherwise with or without a suitable binder. The total level of nitrided mixed oxides, cations and anions and binder may be the same as set out herein.

However, a distinction should be drawn between a metal compound according to the invention and a monolayer of a metal compound on a metal oxide support or a nitrogen containing support where one or more components, metal $M^1/M^2$ and/or oxygen and/or nitrogen is provided by the surface compound and the other components, metal $M^2/M^1$ and/or nitrogen and/or oxygen is provided by the support. Such a monolayer arrangement is not a catalyst according to the present invention but rather a different catalyst which is supported. In this arrangement, the elements $M^1$, $M^2$, N and O do not form a catalyst according to the invention throughout the catalyst material. The surface coating will consist of multiple layers and the layers other than the monolayer will not conform to the invention.

As mentioned above, although at least one metal of the type $M^1$ and one metal of the type $M^2$ are present in the catalyst, further metals or metal cations of the type $M^3$ may also be present in the mixed metal oxide. Typically, when present, the at least one metal $M^3$ whether in the form of a cation or otherwise may form between 0.01 and 10 mol % of the total metal present, more preferably, 0.01-5 mol % of the total metal present, most preferably, 0.1-3 mol % of the total metal present in the metal oxide. Suitable $M^3$ metals include metals from group I of the periodic table, more preferably, lithium, sodium, potassium, rubidium and/or caesium.

Preferably, no other metal types are present in the metal oxide catalyst compound of the present invention above a total other metal level of 0.1 mol % other than the types $M^1$, $M^2$ and optionally $M^3$ as all defined herein, more typically, no other metal types are present in the metal oxide catalyst compound of the present invention above a trace level than the types $M^1$, $M^2$ and optionally $M^3$ as all defined herein.

Typically, it is possible to include two or more metals of the type $M^1$ and/or $M^2$ within the scope of the present invention, more typically, up to three metals of each type $M^1$ and/or $M^2$, most typically, up to two metals of each type $M^1$ and/or $M^2$, especially, up to two metals of one type and only one metal of the other type, more especially, only one metal of each type $M^1$ and $M^2$: all the above being possible with or without any one or more metals of the type $M^3$.

Preferably, including the at least one $M^1$ and $M^2$ metal, the metal oxide compound may have up to four or more preferably up to three metal cations in total, most preferably, however, there are only two metal cations in the metal oxide. Therefore, it is especially preferred that the metal oxide compound consists of one or two each, more especially, one each of the metal cations $M^1$ and $M^2$ together with oxygen anions.

A further preferred formula for the nitrided metal oxide is therefore $M^1{}_n M^2{}_m M^3{}_q O_p N_s$ wherein $M^1$ is a cation, preferably, a 3+ cation and $M^2$ is a cation, preferably, a 5+ cation, n, m, p and s may be a positive integer or decimal number and q may be a positive integer or decimal number or zero. Generally, n and m may independently be between 0.1 and 20, more preferably, between 0.1 and 10, most preferably, between 0.1 and 5 whereas s is the required molecular level of nitridation and p is a number which provides the balance to the remaining positive charge provided by n and m which is not balanced by s. Generally, q may be between 0 and 20, more preferably, 0.1 and 10, most preferably, 0.1 and 5. In a particularly preferred formula n and m are both 1. For the avoidance of doubt, the values on n, m and q defined above are also the total relative number for $M^1$, $M^2$, $M^3{}_{type}$ metals if more than one cation of each type is present.

Generally, the nitrided metal oxide of the present invention is a neutral molecule and therefore the negatively charged oxygen and nitrogen anions and optionally, any other non-metals balance the positively charged metals present.

Preferably, the mole ratio of oxygen to nitrogen in the nitrided mixed metal oxide is in the range 1:1 to 400:1, more preferably, 2:1 to 100:1, most preferably, 3:1 to 40:1.

Preferably, the level of nitrogen in the nitrided mixed metal oxide is in the range 0.1 to 50 wt %, more preferably, 0.5 to 20 wt %, most preferably, 1 to 15 wt %. However, it will be appreciated that the wt % of nitrogen and oxygen in the nitrided mixed metal oxide will depend on the molecular weight of the metals selected.

Preferably, the nitrided mixed oxide consists of the metal cations $M^1$ and $M^2$ and oxygen and nitrogen anions. For the avoidance of doubt, generally, only a single metal of each type is present. However, it is also possible to include two or more metals of the type $M^1$ and/or $M^2$ within the context of the present invention.

As mentioned herein, the term nitrided metal oxide should be understood in the general chemical sense as an ionic or covalent compound having the general formula $(M^1)_n (M^2)_m (M^3)_q O_p N_s$ wherein n and m must be greater than 0 and can take a decimal value and q is independently greater than or equal to 0 and can also take a decimal value. Generally, a mainly ionic compound is formed by the nitrided metal oxides of the present invention. The metal oxide compound itself of the present invention should not be understood in any non-conventional sense as relating to an admixture of metals and/or nitrides, oxides which do not form new nitrided oxide compounds as defined herein.

The mole ratio of $M^1$ to $M^2$ type is generally in the range 10:1 to 1:10, more preferably, 5:1 to 1:5, most preferably, 3:1 to 1:3, especially, 2:1 to 1:2, more especially approximately 1:1. It will be appreciated that oxygen and nitrogen will generally be present at a level to balance the total cationic charge.

The mixed metal oxide compound may be supported on a suitable support such as silica, silicon nitride, colloidal silica, alumina, titania or aluminium phosphate. The support may or may not be an alkali metal doped support. If the support is alkali metal doped, the alkali metal doping agent may be selected from one or more of caesium, potassium, sodium, or lithium, preferably, caesium or potassium, more preferably, caesium. Alternatively, the mixed oxide may itself be doped with any one or more of the above mentioned doping metals representing $M^3$, particularly those of group I above.

Preferably, when a separate support for the catalyst of the first or second aspect is used, the weight ratio of catalyst: support is in the range 10:1 to 1:50, more preferably, 1:1 to 1:20, most preferably, 2:3 to 1:10.

Advantageously, unsaturated ester selectivity is increased by doping cations having a low charge to radius ratio thus caesium was found to be more selective than lithium. Preferably, therefore, if used, the doping metal cation is caesium, rubidium and/or potassium, more preferably, rubidium and/or caesium, most preferably caesium.

Preferably, the carboxylic acid or ester reactant of the present invention is of formula $R^3$—$CH_2$—$COOR^4$ wherein $R^4$ is either hydrogen or an alkyl group and $R^3$ is either hydrogen, an alkyl or aryl group.

According to a further aspect of the present invention there is provided a production process for the manufacture of ethylenically unsaturated carboxylic acids or esters thereof, preferably, an α, β ethylenically unsaturated carboxylic acid or ester, comprising the steps of contacting an alkanoic acid or ester of the formula $R^3$—$CH_2$—$COOR^4$ with formaldehyde or a suitable source thereof, optionally in the presence of an alcohol, wherein $R^3$ and $R^4$ are each independently hydrogen or an alkyl group and $R^3$ may also be an aryl group, in the presence of a catalyst effective to catalyse the reaction, wherein the catalyst is in accordance with the first aspect of the present invention.

A suitable source of formaldehyde may be a compound of formula I

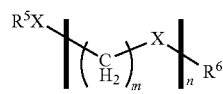

wherein $R^5$ and $R^6$ are independently selected from $C_1$-$C_{12}$ hydrocarbons or H, X is O, n is an integer from 1 to 100, and m is 1.

Preferably, $R^5$ and $R^6$ are independently selected from $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H. Preferably, n is an integer from 1 to 10, more preferably 1 to 5, especially, 1-3.

However, other sources of formaldehyde may be used including trioxane.

Therefore, a suitable source of formaldehyde includes any equilibrium composition which may provide a source of formaldehyde. Examples of such include but are not restricted to methylal (1,1 dimethoxymethane), trioxane, polyoxymethylenes $R^1$—O—$(CH_2$—O$)_i$—$R^2$ wherein $R^1$ and/or $R^2$ are alkyl groups or hydrogen, i=1 to 100, paraformaldehyde, formalin (formaldehyde, methanol, water) and other equilibrium compositions such as a mixture of formaldehyde, methanol and methyl propionate.

Typically, the polyoxymethylenes are higher formals or hemiformals of formaldehyde and methanol $CH_3$—O—$(CH_2$—O$)_i$—$CH_3$ ("formal-i") or $CH_3$—O—$(CH_2$—O$)_i$—H ("hemiformal-i"), wherein i=1 to 100, preferably, 1-5, especially 1-3, or other polyoxymethylenes with at least one non methyl terminal group. Therefore, the source of formaldehyde may also be a polyoxymethylene of formula $R^{31}$—O—$(CH2$-$O$—$)_i R^{32}$, where $R^{31}$ and $R^{32}$ may be the same or different groups and at least one is selected from a $C_2$-$C_{10}$ alkyl group, for instance $R^{31}$=isobutyl and $R^{32}$=methyl.

Preferably, the suitable source of formaldehyde is selected from methylal, higher hemiformals of formaldehyde and methanol, $CH_3$—O—$(CH_2$—O$)_i$—H where i=2, formalin or a mixture comprising formaldehyde, methanol and methyl propionate.

Preferably, by the term formalin is meant a mixture of formaldehyde:methanol:water in the ratio 25 to 65%:0.01 to 25%:25 to 70% by weight. More preferably, by the term formalin is meant a mixture of formaldehyde:methanol:water in the ratio 30 to 60%:0.03 to 20%:35 to 60% by weight. Most preferably, by the term formalin is meant a mixture of formaldehyde:methanol:water in the ratio 35 to 55%:0.05 to 18%:42 to 53% by weight.

Preferably, the mixture comprising formaldehyde, methanol and methyl propionate contains less than 5% water by weight. More preferably, the mixture comprising formaldehyde, methanol and methyl propionate contains less than 1% water by weight. Most preferably, the mixture comprising formaldehyde, methanol and methyl propionate contains 0.1 to 0.5% water by weight.

Preferably, the ethylenically unsaturated acid or ester produced by the process of the invention is selected from methacrylic acid, acrylic acid, methyl methacrylate, ethyl acrylate or butyl acrylate; more preferably, it is an ethylenically unsaturated ester, most preferably, methyl methacrylate.

The process of the invention is particularly suitable for the production of acrylic, alkacrylic, 2-butenoic, cyclohexenoic, maleic, itaconic and fumaric acids and their alkyl esters. Suitable, alkacrylic acids and their esters are ($C_{0-8}$alk) acrylic acid or alkyl ($C_{0-8}$alk)acrylates, typically from the reaction of the corresponding alkanoic acid or ester thereof with a methylene source such as formaldehyde in the presence of the catalyst, preferably the production of methacrylic acid or especially methyl methacrylate (MMA) from propanoic acid or methyl propionate respectively.

The reaction of the present invention may be a batch or continuous reaction.

The term "alkyl" when used herein, means, unless otherwise specified, $C_1$ to $C_{12}$ alkyl and includes methyl, ethyl, ethenyl, propyl, propenyl butyl, butenyl, pentyl, pentenyl, hexyl, hexenyl and heptyl groups, preferably, methyl, ethyl, propyl, butyl, pentyl and hexyl. Unless otherwise specified, alkyl groups may, when there is a sufficient number of carbon atoms, be linear or branched, be cyclic, acyclic or part cyclic/acyclic, be unsubstituted, substituted or terminated by one or more substituents selected from halo, cyano, nitro, —$OR^{19}$, —$OC(O)R^{20}$, —$C(O)R^{21}$, —$C(O)OR^{22}$, —$NR^{23}R^{24}$, —$C(O)NR^{25}R^{26}$, —$SR^{29}$, —$C(O)SR^{30}$, —$C(S)NR^{27}R^{28}$, unsubstituted or substituted aryl, or unsubstituted or substituted Het, wherein $R^{19}$ to $R^{30}$ here and generally herein each independently represent hydrogen, halo, unsubstituted or substituted aryl or unsubstituted or substituted alkyl, or, in the case of $R^{21}$, halo, nitro, cyano and amino and/or be interrupted by one or more (preferably less than 4) oxygen, sulphur, silicon atoms, or by silano or dialkylsilcon groups, or mixtures thereof. Preferably, the alkyl groups are unsubstituted, preferably, linear and preferably, saturated.

The term "alkenyl" should be understood as "alkyl" above except at least one carbon carbon bond therein is unsaturated and accordingly the term relates to $C_2$ to $C_{12}$ alkenyl groups.

The term "alk" or the like should, in the absence of information to the contrary, be taken to be in accordance with the above definition of "alkyl" except "$C_0$ alk" means non-substituted with an alkyl.

The term "aryl" when used herein includes five-to-ten-membered, preferably five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro, cyano or amino.

The term "halo" when used herein means a chloro, bromo, iodo or fluoro group, preferably, chloro or fluoro.

Without prejudice to the scope of protection and without being bound by theory, upon making this surprising discovery, the inventors tested whether there may be a diene impurity that was causing the colouration. However, reaction with the dienophile does not seem to affect the diene impurities identified, indicating that the impurity may not be a diene.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —$OR^{19}$, —$OC(O)R^{20}$, —$C(O)R^{21}$, —$C(O)OR^{22}$, —$N(R^{23})R^{24}$, —$C(O)N(R^{25})R^{26}$, $SR^{29}$, —$C(O)SR^{30}$ or —$C(S)N(R^{27})R^{28}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

Suitable optional alcohols for use in the catalysed reaction of the present invention may be selected from a $C_1$-$C_{30}$ alkanol, including aryl alcohols, which may be optionally substituted with one or more substituents selected from alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)NR^{27}R^{28}$, $SR^{29}$ or $C(O)SR^{30}$ as defined herein. Highly preferred alkanols are $C_1$-$C_8$ alkanols such as methanol, ethanol, propanol, iso-propanol, iso-butanol, t-butyl alcohol, phenol, n-butanol and chlorocapryl alcohol. Although the monoalkanols are most preferred, poly-alkanols, preferably, selected from di-octa ols such as diols, triols, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl) ethane, nannose, sorbase, galactose and other sugars. Preferred sugars include sucrose, fructose and glucose. Especially preferred alkanols are methanol and ethanol. The most preferred alkanol is methanol. The amount of alcohol is not critical. Generally, amounts are used in excess of the amount of substrate to be esterified. Thus the alcohol may serve as the reaction solvent as well, although, if desired, separate or further solvents may also be used.

It will be appreciated that the end product of the reaction is determined at least in part by the source of alkanol used. For instance, use of methanol produces the corresponding methyl ester.

Typical conditions of temperature and pressure in the process of the invention are between 100° C. and 400° C., more preferably, 200° C. and 375° C., most preferably, 300° C. and 360° C.; between 0.001 MPa and 1 MPa, more preferably, 0.03 MPa and 0.5 MPa, most preferably, between 0.03 MPa and 0.3 MPa.

Contact times for the reactants in the presence of the catalyst are dependent on temperature, pressure, the nature of any support and the concentration of the catalyst with respect to any support but are typically between 0.05 and 300 secs, more preferably, 0.1 and 240 secs, most preferably, 0.5 and 120 secs, especially, 1 and 40 secs.

The amount of catalyst used in the process of the present invention is not necessarily critical and will be determined by the practicalities of the process in which it is employed. However, the amount of catalyst will generally be chosen to effect the optimum selectivity and yield. Nevertheless, the skilled person will appreciate that the minimum amount of catalyst should be sufficient to bring about effective catalyst surface contact of the reactants during the contact time. In addition, the skilled person would appreciate that there would not really be an upper limit to the amount of catalyst relative to the reactants but that in practice this may be governed again by the contact time required.

The relative amount of reagents in the process of the invention can vary within wide limits but generally the mole ratio of formaldehyde or suitable source thereof to the carboxylic acid or ester is within the range of 20:1 to 1:20, more preferably, 5:1 to 1:15, The most preferred ratio will depend on the form of the formaldehyde and the ability of the catalyst to liberate formaldehyde from the formaldehydic species. Thus highly reactive formaldehydic substances where one or both of $R^{31}$ and $R^{32}$ in $R^{31}O$—$(CH_2$—$O$—$)_iR^{32}$ is H require relatively low ratios, typically, in this case, the mole ratio of formaldehyde or suitable source thereof to the carboxylic acid or ester is within the range of 1:1 to 1:9. Where neither of $R^{31}$ and $R^{32}$ is H, as for instance in $CH_3O$—$CH_2$—$OCH_3$, or in trioxane higher ratios are most preferred, typically, 3:1 to 1:3.

As mentioned above, due to the source of formaldehyde, water may also be present in the reaction mixture. Depending on the source of formaldehyde, it may be necessary to remove some or all of the water therefrom prior to catalysis. Maintaining lower levels of water than that in the source of formaldehyde may be advantageous to the catalytic efficiency and/or subsequent purification of the products. Water at less than 10 mole % in the reactor is preferred, more preferably, less than 5 mole %, most preferably, less than 2 mole %.

The molar ratio of alcohol to the acid or ester is typically within the range 20:1 to 1:20, preferably 10:1 to 1:10, most preferably 5:1 to 1:5, for example 1:1. However the most preferred ratio will depend on the amount of water fed to the catalyst in the reactants plus the amount produced by the reaction, so that the preferred molar ratio of the alcohol to the total water in the reaction will be at least 1:1 and more preferably at least 3:1.

The reagents may be fed to the reactor independently or after prior mixing and the process of reaction may be continuous or batch. Preferably, however, a continuous process is used.

Typically, the reaction takes place in the gas phase. Accordingly, suitable condensing equipment is generally required to condense the product stream after reaction has taken place. Similarly, a vaporiser may be used to bring the reactants up to temperature prior to the catalyst bed.

DETAILED DESCRIPTION

It is to be understood by a person having ordinary skill in the art that the present discussion is a description of exemplary embodiments only and is not intended as limiting the broader aspects of the present invention. The following example is provided to further illustrate the invention and is not to be construed to unduly limit the scope of the invention. Embodiments of the invention will now be described with reference to the following non-limiting examples and by way of illustration only.

EXPERIMENTAL

TABLE 1

| | Catalyst | Contact time [s] | MMA + MAA yield [%] | MAA selectivity [%] | MMA + MAA selectivity [%] | MAA + MAA yield/s |
|---|---|---|---|---|---|---|
| Comp Ex. 1 | AlPO | 5.20 | 4.9 | 10.4 | 59.3 | 0.9 |
| Comp Ex. 1 | AlPO | 1.47 | 4.8 | 12.9 | 78.0 | 3.3 |
| Ex. 1 | AlPON 03750 | 1.47 | 3.1 | 13.4 | 95.2 | 2.1 |
| Ex. 1 | AlPON 03750 | 5.20 | | | | |
| Ex. 2 | AlPON 06750 | 5.20 | 7.6 | 16.5 | 92.4 | 1.5 |
| Ex. 3 | AlPON 15750 | 5.20 | 8.1 | 17.3 | 93.5 | 1.6 |

Comparative Example 1 AlPO

The acid catalyst that provided the base substrate for modification was an amorphous aluminium phosphate (AlPO) prepared by a sol-gel method involving co-gelation from a solution containing the component salts.

Co-Gelation Method

A high surface-area amorphous aluminium phosphate was prepared by co-gelation of a solution of salts containing the elements aluminium and phosphorus.

37.5 g of aluminium nitrate nonahydrate $Al(NO_3)_3 \cdot 9H_2O$ and 13.2 g of diammonium hydrogen phosphate $(NH_4)_2HPO_4$ were dissolved together in 160 ml of demineralised water acidified with nitric acid $HNO_3$. Solution of ammonium hydroxide was added until pH 7 was reached. Formed hydrogel was mixed for further 1 hr, after that it was filtered and washed with water. It was dried at 80° C. overnight and then calcined in air at 600° C. for 1 hr. The calcined product was sieved to retain granules (0.5-1.4 mm in diameter) for a catalyst testing.

Catalyst testing: 3 g of a catalyst was placed in a stainless steel tubular reactor connected to a vaporiser. The reactor was heated to 350° C. and vaporiser to 300° C. The mixture of 56.2 mole % of methyl propionate, 33.7 mole % of methanol, 9.6 mole % of formaldehyde and 0.5 mole % of water was passed through. The condensed reaction mixture was analysed by gas chromatography equipped with CP-Sil 1701 column.

Example 1 AlPON 03750

Approximately 7 g of granule product from comparative example 1 were placed in an alumina boat in the centre of a tube furnace and heated at 5° C./min ramp in a flow of dry nitrogen at the rate of 150 ml/min. At 600° C. the gas feed was switched to dry ammonia at a rate of 150 ml/min while continuing to heat to 750° C. and maintained at this temperature for 3 hrs before the feed gas was switched back to dry nitrogen (150 ml/min). The furnace was allowed to cool to below 100° C. before sample recovery from the dry atmosphere.

Catalyst was tested as described in comparative example 1.

Example 2 AlPON 06750

Catalyst was prepared as in example 1, except that instead of 3 hrs of ammonia treatment 6 hrs were applied.

Catalyst was tested as described in comparative example 1.

Example 3 ALPON15750

Catalyst was prepared as in example 1, except that instead of 3 hrs of ammonia treatment 15 hrs was applied.

Catalyst was tested as described in comparative example 1.

Comparative Example 2 ZrPO 7.9 g of diammonium hydrogen phosphate $(NH_4)_2HPO_4$ dissolved in 50 ml of demineralised water were added dropwise to 19.3 g of zirconium oxychloride $ZrOCl_2 \cdot 8H_2O$ dissolved in 200 ml of demineralised water acidified with nitric acid $HNO_3$ and stirred for 2 hrs. It was filtered and washed with water, then dried at 110° C. overnight and calcined in air at 550° C. for 1 hr. Catalyst was tested as described in comparative example 1.

Example 4 ZrPON 03750

Approximately 7 g of granule product from comparative example 2 were placed in an alumina boat in the centre of a tube furnace and heated at 5° C./min ramp in a flow of dry nitrogen at the rate of 150 ml/min. At 600° C. the gas feed was switched to dry ammonia at a rate of 150 ml/min while continuing to heat to 750° C. and maintained at this temperature for 3 hrs before the feed gas was switched back to dry nitrogen (150 ml/min). The furnace was allowed to cool to below 100° C. before sample recovery from the dry atmosphere.

Catalyst was tested as described in comparative example 1.

Comparative Example 3 SnPO 13.0 g of tin chloride $SnCl_4$ in 200 ml of demineralised water was heated to 50° C. and stirred with a magnetic bar while adding dropwise 7.1 g of diammonium hydrogen phosphate $(NH_4)_2HPO_4$ dissolved in 300 ml of demineralised water. The mixing was continued for 2 hrs. After that the product was filtered and washed with water. It was dried at 110° C. overnight and then calcined in air at 400° C. for 1 hr.

Catalyst was tested as described in comparative example 1.

Example 5 SnPON 06400

Approximately 7 g of granule product from comparative example 3 were placed in an alumina boat in the centre of a tube furnace and heated at 5° C./min ramp in a flow of dry nitrogen at the rate of 150 ml/min. At 250° C. the gas feed was switched to dry ammonia at a rate of 150 ml/min while continuing to heat to 400° C. and maintained at this temperature for 6 hrs before the feed gas was switched back to dry nitrogen (150 ml/min). The furnace was allowed to cool to below 100° C. before sample recovery from the dry atmosphere.

Catalyst was tested as described in comparative example 1.

TABLE 2

| | Catalyst | Contact time [s] | MMA + MAA yield [%] | MAA selectivity [%] | MMA + MAA selectivity [%] | MMA + MAA yield/s |
|---|---|---|---|---|---|---|
| Comp Ex. 2 | ZrPO | 0.41 | 4.04 | 7.5 | 64.6 | 9.8 |
| Ex. 4 | ZrPON 03750 | 0.41 | 4.55 | 7.4 | 71.6 | 11.1 |
| Comp Ex. 3 | SnPO | 2.00 | 2.1 | 11.0 | 64.3 | 1.0 |
| Ex. 5 | SnPON 06400 | 3.05 | 2.1 | 0.3 | 86.4 | 0.7 |

TABLE 3

| | Catalyst | Contact time [s] | MMA + MAA yield [%] | MAA selectivity [%] | MMA + MAA selectivity [%] | MMA + MAA yield/s |
|---|---|---|---|---|---|---|
| Comp Ex. 4 | ZrNbO | 0.6 | 5.5 | 3.8 | 80.6 | 9.2 |
| Comp Ex. 5 | GaSbO | 1.12 | 6.5 | 1.9 | 77.8 | 5.8 |

Comparative Example 4 ZrNbO 10.1 g of niobium chloride $NbCl_5$ in 25 ml of demineralised water acidified with nitric acid $HNO_3$ were added to 12.1 g of zirconium oxychloride $ZrOCl_2 \cdot 8H_2O$ in 25 ml of demineralised water acidified with nitric acid $HNO_3$ while stirring. After that a solution of ammonium hydroxide was added until pH 7 was reached. This was aged for 1 hr, and then it was filtered and washed with copious amount of water. It was dried at 80° C. overnight and then calcined in air at 600° C. for 1 hr.

Catalyst was tested as described in comparative example 1.

Example 6 ZrNbON 06400

Approximately 7 g of granule product from comparative example 4 were placed in an alumina boat in the centre of a tube furnace and heated at 5° C./min ramp in a flow of dry nitrogen at the rate of 150 ml/min. At 250° C. the gas feed was switched to dry ammonia at a rate of 150 ml/min while continuing to heat to 400° C. and maintained at this temperature for 6 hrs before the feed gas was switched back to dry nitrogen (150 ml/min). The furnace was allowed to cool to below 100° C. before sample recovery from the dry atmosphere.

Catalyst was tested as described in comparative example 1 and found to have improved selectivity.

Comparative Example 5 GaSbO 5 g of gallium chloride $GaCl_3$ in 25 ml of demineralised water acidified with nitric acid $HNO_3$ were added dropwise to 8.6 g of antimony chloride $SbCl_5$ in 5 ml of demineralised water while stirring. Subsequently a solution of ammonium hydroxide was added until pH 7 was reached. The reaction mixture was aged for 1 hr, after that it was filtered and washed with copious amount of water. It was dried at 80° C. overnight and then calcined in air at 600° C. for 1 hr. Catalyst was tested as described in comparative example 1.

Example 7 GaSbON 06400

Approximately 7 g of granule product from comparative example 5 were placed in an alumina boat in the centre of a tube furnace and heated at 5° C./min ramp in a flow of dry nitrogen at the rate of 150 ml/min. At 250° C. the gas feed was switched to dry ammonia at a rate of 150 ml/min while continuing to heat to 400° C. and maintained at this temperature for 6 hrs before the feed gas was switched back to dry nitrogen (150 ml/min). The furnace was allowed to cool to below 100° C. before sample recovery from the dry atmosphere.

Catalyst was tested as described in comparative example 1 and found to have improved selectivity.

Comparative Example 6 Ga0.1Al0.9PO 5 g of gallium chloride, 34 g of aluminium chloride $AlCl_3$ were mixed with 19.4 g of phosphoric acid $H_3PO_4$ in 122 ml of demineralised water. This was cooled to 0° C. in a dry ice alcohol bath. Subsequently a large excess of propylene oxide was slowly added under vigorous stirring. The solution turned into a translucent gel after a few hours. The product was washed with isopropanol. It was dried at 110° C. overnight and then calcined in air at 650° C. for 1 hr. Catalyst was tested as described in comparative example 1.

Example 8 Ga0.1Al0.9PON 03750

Approximately 7 g of granule product from comparative example 6 were placed in an alumina boat in the centre of a tube furnace and heated at 5° C./min ramp in a flow of dry nitrogen at the rate of 150 ml/min. At 600° C. the gas feed was switched to dry ammonia at a rate of 150 ml/min while continuing to heat to 750° C. and maintained at this temperature for 3 hrs before the feed gas was switched back to dry nitrogen (150 ml/min). The furnace was allowed to cool to below 100° C. before sample recovery from the dry atmosphere.

Catalyst was tested as described in comparative example 1.

Example 9 Ga0.1Al0.9PON 15750

Catalyst was prepared as in example 8, except that instead of 3 hrs of ammonia treatment 15 hrs was applied.

Catalyst was tested as described in comparative example 1.

TABLE 4

| | Catalyst | Contact time [s] | MMA + MAA yield [%] | MAA selectivity [%] | MMA + MAA selectivity [%] | MAA + MAA yield/s |
|---|---|---|---|---|---|---|
| Comp. Ex. 6 | $Ga_{0.1}Al_{0.9}PO$ | 2.40 | 4.3 | 10.4 | 64.1 | 1.8 |
| Ex. 8 | $Ga_{0.1}Al_{0.9}PON$ 03750 | 2.36 | 6.4 | 11.7 | 75.2 | 2.7 |
| Ex. 9 | $Ga_{0.1}Al_{0.9}PON$ 15750 | 2.32 | 5.5 | 4.9 | 80.9 | 2.4 |

TABLE 5

| | Catalyst | Contact time [s] | MMA + MAA yield [%] | MAA selectivity [%] | MMA + MAA selectivity [%] | MMA + MAA yield/s |
|---|---|---|---|---|---|---|
| Comp. Ex. 7 | $ZrO_2$ | 0.89 | 5.8 | 1.5 | 50.9 | 6.5 |
| Comp. Ex. 8 | ZrON 15500 | 4.58 | 5.7 | 0.5 | 50.0 | 1.2 |
| Comp. Ex. 9 | $SiO_2$ | 10.03 | 0.15 | — | — | 0.015 |
| Comp. Ex. 10 | SiON (Grace) 15400 | 14.57 | 0.6 | — | — | 0.04 |
| Comp. Ex. 11 | SiON (Grace) 15750 | 8.53 | 0.6 | — | — | 0.07 |

TABLE 5-continued

| | Catalyst | Contact time [s] | MMA + MAA yield [%] | MAA selectivity [%] | MMA + MAA selectivity [%] | MMA + MAA yield/s |
|---|---|---|---|---|---|---|
| Comp. Ex. 12 | Al$_2$O$_3$ | 4.0 | 5.6 | 6.3 | 64.0 | 10.2 |
| Comp. Ex. 13 | AlON 03750 | 5.6 | 5.6 | 7.6 | 60.0 | 10.4 |

Comparative Example 7 ZrO$_2$ 14.5 g of zirconium oxychloride octahydrate ZrOCl$_2$.8H$_2$O were dissolved in 300 ml of demineralised water and stirred continuously while adding 10 ml of 30% ammonia in 110 ml of water. The suspension was agitated at room temperature for 3 hrs, then filtered and washed with water to remove any residues of chloride. The product was dried at 80° C. overnight and calcined at 500° C. for 1 hr.

Catalyst was tested as described in comparative example 1.

Comparative Example 8 ZrON 15500

Approximately 7 g of granule product from comparative example 7 were placed in an alumina boat in the centre of a tube furnace and heated at 5° C./min ramp in a flow of dry nitrogen at the rate of 150 ml/min. At 350° C. the gas feed was switched to dry ammonia at a rate of 150 ml/min while continuing to heat to 500° C. and maintained at this temperature for 15 hrs before the feed gas was switched back to dry nitrogen (150 ml/min). The furnace was allowed to cool to below 100° C. before sample recovery from the dry atmosphere.

Catalyst was tested as described in comparative example 1.

Comparative Example 9 SiO$_2$

Pure SiO$_2$ beads were purchased from Grace.
Catalyst was tested as described in comparative example 1.

Comparative Example 10 SiON (Grace) 15400

Approximately 7 g of granule product from comparative example 9 were placed in an alumina boat in the centre of a tube furnace and heated at 5° C./min ramp in a flow of dry nitrogen at the rate of 150 ml/min. At 250° C. the gas feed was switched to dry ammonia at a rate of 150 ml/min while continuing to heat to 400° C. and maintained at this temperature for 15 hrs before the feed gas was switched back to dry nitrogen (150 ml/min). The furnace was allowed to cool to below 100° C. before sample recovery from the dry atmosphere.

Catalyst was tested as described in comparative example 1.

Comparative Example 11 SiON (Grace) 15750

Approximately 7 g of granule product from comparative example 9 were placed in an alumina boat in the centre of a tube furnace and heated at 5° C./min ramp in a flow of dry nitrogen at the rate of 150 ml/min. At 600° C. the gas feed was switched to dry ammonia at a rate of 150 ml/min while continuing to heat to 750° C. and maintained at this temperature for 15 hrs before the feed gas was switched back to dry nitrogen (150 ml/min). The furnace was allowed to cool to below 100° C. before sample recovery from the dry atmosphere.

Catalyst was tested as described in comparative example 1.

Comparative Example 12 Al$_2$O$_3$ 75.0 g of aluminium nitrate were dissolved in demineralised water, which was acidified with drops of nitric acid to aid dissolution. The gel was precipitated by addition of aqueous ammonia. The gel was filtered and washed with water. After drying overnight at 110° C., it was calcined at 500° C. in air flow for 1 hr.

Catalyst was tested as described in comparative example 1.

Comparative Example 13 AlON 03750

Approximately 7 g of granule product from comparative example 12 were placed in an alumina boat in the centre of a tube furnace and heated at 5° C./min ramp in a flow of dry nitrogen at the rate of 150 ml/min. At 600° C. the gas feed was switched to dry ammonia at a rate of 150 ml/min while continuing to heat to 750° C. and maintained at this temperature for 3 hrs before the feed gas was switched back to dry nitrogen (150 ml/min). The furnace was allowed to cool to below 100° C. before sample recovery from the dry atmosphere.

Catalyst was tested as described in comparative example 1.

Several examples were tested for the generation of side products in the condensed reaction mixture. Three side products that may prove problematic during separation in an industrial process due to their being close in boiling point to one of the desired end products, methyl methacrylate, were tested. These are toluene, diethyl ketone and methyl isobutyrate. The results are shown in table 6 and show a marked reduction in such impurities for the nitrided mixed oxides compared with both non-nitrided mixed oxides and nitrided single metal oxides.

TABLE 6

| | Catalyst | Contact time [s] | MIB [mole %] | DEK [mole %] | toluene [mole %] |
|---|---|---|---|---|---|
| Comp. Ex. 1 | AlPO | 1.83 | 0.0240 | 0.0547 | 0.0054 |
| Ex. 1 | AlPON 03750 | 1.47 | 0.0013 | 0.0031 | 0.0003 |
| Ex. 2 | AlPON 06750 | 5.20 | 0.0126 | 0.0038 | 0.0008 |
| Comp. Ex. 2 | ZrPO | 0.42 | 0.0228 | 0.0569 | 0.0042 |
| Ex. 4 | ZrPON 03750 | 0.41 | 0.0150 | 0.0370 | 0.0028 |
| Comp. Ex. 7 | ZrO2 | 1.01 | 0.1819 | 0.7004 | 0.0001 |
| Comp. Ex. 8 | ZrON 15500 | 4.70 | 0.2591 | 0.8241 | 0.0001 |

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. A method of producing an ethylenically unsaturated carboxylic acid or ester comprising the steps of contacting formaldehyde or a source thereof with a carboxylic acid or ester of formula $R^3$—$CH_2$—$COOR^4$ wherein $R^4$ is either hydrogen or an alkyl group and $R^3$ is either hydrogen, an alkyl or an aryl group, in the presence of a catalyst and optionally in the presence of an alcohol, wherein the catalyst comprises a nitrided metal oxide having at least two metal cations, $M^1$ and $M^2$, wherein:
the $M^1$ type of metal is selected from one or more metals in the list consisting of:—B, Al, Ga, In, Tl, Si, Ge, Sn, Pb, Ti, Zr, Hf and Rf, and
the $M^2$ type of metal is selected from one or more metals in the list consisting of:—P(5+), Nb(5+), As(5+), Sb(5+) and Ta(5+).

2. A method according to claim 1, wherein the nitrided metal oxide consists of two to four metal cations, and oxygen and nitrogen anions.

3. A method according to claim 1, wherein the nitrided metal oxide is selected from the list consisting of:—AlPON; ZrPON; SnPON; ZrNbON; GaSbON; and GaAlPON, either unsupported or supported on a support, the support comprising alumina, silica, silicon nitride, colloidal silica, titania or aluminium phosphate.

4. The method of claim 1, wherein the nitrided metal oxide is supported on a support selected from the group consisting of: alumina, silica, silicon nitride, colloidal silica, titania or aluminium phosphate.

5. A method according to claim 1, wherein the ethylenically unsaturated acid or ester produced by the process of the invention is selected from methacrylic acid, acrylic acid, methyl methacrylate, ethyl acrylate or butyl acrylate.

6. The method of claim 1, wherein the step of contacting formaldehyde with a carboxylic acid or ester in the presence of a catalyst is also carried out in the presence of alcohol.

7. The method of claim 1, wherein the ethylenically unsaturated carboxylic acid or ester is produced with a catalyst system by contacting formaldehyde or a source thereof with a carboxylic acid or ester of formula $R^3$—$CH_2$—$COOR^4$ wherein $R^4$ is either hydrogen or an alkyl group and $R^3$ is either hydrogen, an alkyl or an aryl group, in the presence of a catalyst of the catalyst system, wherein the catalyst comprises a nitrided metal oxide having at least two metal cations, $M^1$ and $M^2$, wherein:
the $M^1$ type of metal is selected from one or more metals in the list consisting of:—B, Al, Ga, In, Tl, Si, Ge, Sn, Pb, Ti, Zr, Hf and Rf, and
the $M^2$ type of metal is selected from one or more metals in the list consisting of:—P(5+), Nb(5+), As (5+) Sb(5+) and Ta(5+) to produce the ethylenically unsaturated carboxylic acid or ester.

8. The method of claim 1, wherein the ethylenically unsaturated carboxylic acid or ester is an $\alpha,\beta$ ethylenically unsaturated acid.

* * * * *